(12) United States Patent
Wenz

(10) Patent No.: US 8,289,509 B2
(45) Date of Patent: Oct. 16, 2012

(54) INSPECTION DEVICE AND INSPECTION METHOD FOR THE OPTICAL EXAMINATION OF OBJECT SURFACES, PARTICULARLY OF WAFER SURFACES

(75) Inventor: Holger Wenz, Ludwigshafen (DE)

(73) Assignee: Nanophotonics AG, Mainz (DE)

( * ) Notice: Subject to any disclaimer, the term of this patent is extended or adjusted under 35 U.S.C. 154(b) by 372 days.

(21) Appl. No.: 12/657,744

(22) Filed: Jan. 27, 2010

(65) Prior Publication Data

US 2010/0195097 A1 Aug. 5, 2010

(30) Foreign Application Priority Data

Jan. 30, 2009 (DE) .......................... 10 2009 000 528

(51) Int. Cl.
*G03B 27/52* (2006.01)

(52) U.S. Cl. ..................................................... 356/237.5

(58) Field of Classification Search ......................... None
See application file for complete search history.

(56) References Cited

U.S. PATENT DOCUMENTS

| 4,004,153 | A |   | 1/1977 | Obser et al. | |
|---|---|---|---|---|---|
| 5,838,433 | A | * | 11/1998 | Hagiwara | ..................... 356/364 |
| 6,788,404 | B2 |   | 9/2004 | Lange | |
| 6,809,809 | B2 | * | 10/2004 | Kinney et al. | ............... 356/237.5 |
| 6,956,644 | B2 |   | 10/2005 | Biellak et al. | |
| 7,061,598 | B1 |   | 6/2006 | Bevis et al. | |
| 7,123,357 | B2 |   | 10/2006 | Meeks | |
| 7,304,310 | B1 |   | 12/2007 | Shortt et al. | |
| 7,630,069 | B2 | * | 12/2009 | Naftali et al. | ............... 356/237.2 |

FOREIGN PATENT DOCUMENTS

| DE | 24 33 682 | 1/1976 |
|---|---|---|
| DE | 698 19 929 T2 | 11/2004 |
| EP | 1257869 B1 | 9/2006 |

* cited by examiner

*Primary Examiner* — Tu Nguyen
(74) *Attorney, Agent, or Firm* — Hudak, Shunk & Farine Co. LPA

(57) ABSTRACT

An inspection device and a method of inspection, for optical examination of object surfaces, particularly wafer surfaces, wherein the object surface is illuminated by a first illumination device and a second illumination device, wherewith the light reflected and/or scattered from irregularities on the object surface is detected by means of a "scattered light detector" operating in the dark field of the first and second illumination devices, and wherewith the object surface is illuminated by a first illumination device and a second illumination device, wherewith the first illumination device has a laser for illuminating a measurement point on the object surface. The second illumination device is disposed (and oriented) to illuminate the same measurement point on the object surface but with a larger image spot, with the use of light of lower coherence and/or with less anisotropy than that of the laser.

20 Claims, 3 Drawing Sheets

INSPECTION DEVICE AND INSPECTION METHOD FOR THE OPTICAL EXAMINATION OF OBJECT SURFACES, PARTICULARLY OF WAFER SURFACES

FIELD OF INVENTION

The invention relates to an inspection device and a method of inspection, for optical examination of object surfaces, particularly wafer surfaces, wherein the object surface is illuminated by a first illumination device and a second illumination device, wherewith the light reflected and/or scattered from irregularities on the object surface is detected by means of a "scattered light detector" operating in the dark field of the first and second illumination devices, and wherewith the first illumination device has a laser for illuminating a measurement point on the object surface.

BACKGROUND OF THE INVENTION

The optical inspection of semiconductor wafers for defects is an important part of the manufacturing process for computer chips. In particular, for examining the upper and lower sides of flat wafers a dark field illumination is employed, for visibilizing the irregularities. This facilitates the search for defects such as scratches, breaks, cracks, or impressions in the surface, or particles on the surface, of the wafer. In the context of the present document, the term "irregularity" is used to refer to any type of defect(s). The desired inspection enables not just a qualitative but also a quantitative evaluation of the surface quality. Accordingly, an inspection device of the general type described supra should be capable of achieving a very fine detection, such that characteristics of each defect type can be determined and the defects found can be classified.

Numerous inspection devices are known which employ various means to achieve the stated objective. In U.S. Pat. No. 7,123,357 B2, for example, various methods are disclosed for classification of surface defects in dark field measurement, employing a plurality of laser beams oriented mutually orthogonally, which beams cross at the object surface, preferably in the radial and circumferential directions of the wafer. The intensities of the scattered light from different laser beams are detected separately and are compared with each other, to garner information about the anisotropy, orientation, and aspect ratios of defects.

U.S. Pat. No. 6,956,644 B2 describes a method of optical surface inspection of wafers in the dark field wherein the surface is illuminated pointwise with two different angles of incidence of the light and/or with two different wavelengths, from a laser, one after the other. The scattered light from the different illumination situations is received by a respective detector, and from the differences in intensity of the scattered light it is concluded whether a detected anomaly on the object surface is a particle on the surface or a so-called "crystal originated particle" (COP). The term COP is historical and it is misleading in that it signifies a defect in the wafer surface and not an actual separate particle.

In U.S. Pat. No. 7,061,598 B2, the inventors take a different approach. In the method for dark field inspection of a wafer surface, an optical element is used to deflect light from a laser which is scattered from a wafer surface (in particular, from an irregularity on the surface), wherewith the light is deflected onto a location-resolving detector such that information about intensity and also scattering angle is obtained which information reveals keys to the type of the defect.

In U.S. Pat. No. 7,304,310 B2, a method is proposed wherein UV light is selectively guided in combination with light of a different wavelength onto a substrate surface of the object sought to be examined. In the dark field inspection the scattered light is measured at different detection angles in combination with different detection wavelengths. In this way it is said that one can distinguish between scattered light and fluorescence light, and one can draw conclusions about the source (on the substrate surface) of the scattered light.

A problem confronting all inspection methods with dark field illumination is that different types of defects have very different physical scattering behavior. This relates to, first, the intensity of the scattered light, which is different for small-surface (point-like) defects or particles and large-surface defects such as scratches or breaks. Secondly, anisotropic defects (which have a primary direction), e.g. scratches or cracks cause the scattered signal to depend sharply on the relative arrangement between the scattered light detector and the light source. Finally, defects having dimensions less than one half of the wavelength of the light used lead, via interference, to a substantial spatial modulation of the scattered light (speckles) and therefore again to strong dependence of the measurement signal on the relative arrangement.

General solutions to reduce such artifacts are disclosed in, e.g., U.S. Pat. No. 6,788,404 B2. In that patent it is proposed to combine a plurality of beams of light sources of different frequencies, in particular a broadband and a narrow-band light source, into a single light beam, and to direct this combined beam to the surface to be examined. In this way, the overall intensity of the light is increased, but interference effects are reduced by the use of the broadband light source, while at the same time the high intensity of the narrow-band light component is exploited.

Another proposed solution is disclosed in the patent EP 1257869 B1. This relates to a device and a method for reducing the abovementioned "laser speckles" when illuminating rough surfaces. With this solution, polarization effects are eliminated by dividing an emitted laser beam into two partial beams of equal intensity but orthogonal polarization. The partial streams are passed through optical paths with oscillating path length differences, and are then collected into a common beam with which the surface is illuminated.

Apart from the fact that the latter two proposed solutions require complex and costly measures relating to the illumination device, they only partly solve the set of problems presented relating to the scattered light.

SUMMARY OF THE INVENTION

Accordingly, the underlying problem of the present invention was to devise an inspection device and an inspection method which by simple means allow defects on object surfaces to be detected and to be classified with relatively high reliability.

This problem is solved by an inspection device and an inspection method with features described in the claims. Advantageous refinements of the invention are set forth in the dependent claims.

According to the invention, the inspection device and method of the type described initially supra are refined in that the second illumination device, with the use of light of less coherence and/or less anisotropy than that of the laser or laser beam, is employed to illuminate the same measurement point on the object surface, with a larger image spot.

The inventor has perceived that different types of defects require different types of illumination in order to achieve detection with maximally possible simultaneous sensitivity and high reproducibility, because of their different physical scattering characteristics. Small-area point-like defects or particles have relatively isotropic reflection and scattering behavior, but due to their small size have relatively low reflection and scattering capability, and accordingly tend to require an illumination source of high intensity. At the same time, they do not require a very large image spot (impinging light beam), and thus (as it turns out) a laser is sufficient as the light source.

Relatively large, anisotropic defects (particularly, large shallow defects or linearly shaped defects) are better detected with a larger image spot (impinging light beam), because with these defects a larger illuminated surface will illuminate a larger portion of the defect. Also, the invention incorporates the concept that with anisotropic defects a dependence of the scattered light signal on the relative arrangement between the illumination device and the detector can be minimized if for such defects illumination with light of relatively low spatial and/or timewise coherence, and/or relatively low anisotropy, is employed, compared to the light from a laser. In this way, one can avoid or at least reduce the abovementioned speckles (thus one can avoid or reduce modulation of the measurement signal in a manner which depends on the orientation). Light of low anisotropy in the context of the invention should be understood in the most general case to mean light which lacks one or more anisotropic characteristics. Anisotropic characteristics may include the shape of the illuminating image spot (particularly the aspect ratio), the degree of polarization of the light, and the direction of the illumination.

Finally, the invention was made with recognition of the fact that, considering the likelihood of interference effects for very small defects having dimensions less than one half the wavelength of the light used, it is not disadvantageous to use coherent illumination for such defects, whereas for larger defects the use of coherent illumination leads to the described orientation-dependence of the intensity of the scattered light and thereby to a random and non-reproducible measurement result.

The invention makes use of all of these concepts, in that it employs two different illumination devices, at least one of which provides optimal illumination for a given class of defect types.

To avoid interference effects such as, e.g., the abovementioned speckles, the second illumination device preferably has a broadband light source.

Advantageously, a second illumination device providing light density 1-100 mW/sq mm on the wafer surface is employed. In comparison, the intensity of the laser illumination on the wafer surface is substantially higher, in particular c. 10,000 mW/sq mm.

Particularly preferably, the second illumination device comprises a plurality of light sources in symmetrical disposition around the image spot and/or in a circular or partial circular disposition around the image spot.

In this way, the illumination comes close to an anisotropic illumination of high light density.

Preferably, the second illumination device comprises one or more light emitting diodes (LEDs) as light source(s).

LEDs are inexpensive and small, and do not generate any appreciable heat, so that they are particularly suitable for the present application in a situation where a plurality of light sources are combined in the second illumination device.

Particularly preferably, the first and second illumination devices have different spectral ranges, and the scattered light detector has a dichroic beam splitter or spectral filter.

In this way, the inspection device may be employed in a so-called "wavelength multiplexing" mode wherein each measurement point is illuminated simultaneously with the first and second illumination device and the scattered light is broken up into the individual (two) spectral parts with the beam splitter or spectral filter, which spectral parts are then measured by various sensors (or parts of sensors).

Alternatively to this, the inspection device has control means which alternately control the first and second illumination device.

In this way, the inspection device may be employed in a so-called "time-multiplexing" mode wherein each measurement point undergoes measurement of the scattered light alternately under illumination with the first and second illumination device.

The separate scattered light intensities in the two channels (which channels are separated by one of the described techniques) are used to form a ratio or the like, which yields information about the extent of the defect.

Thus, in the case of a defect of small extent, the ratio of the scattered light from the first illumination device to that of the second illumination device will be greater than in the case of a defect of relatively large extent.

Further, the scattered light intensities from one or the other channel yield information about the orientation and/or size of the defect. E.g., if one concludes from the ratio of the scattering intensities of the two channels that the defect is a shallow ("flat") defect, one may further conclude from the absolute value of the intensity of the detected scattered light that the value is a product of the size and orientation. This is illustrated by the following example: For a large (and shallow) defect, which produces a detector signal in both channels over numerous measuring points, suppose that the scattered signal from the laser channel varies sharply between neighboring measurement points. One can conclude from this that the defect is comprised of a group (or sequence) of small individual defects, e.g. particles (a so-called "cluster" of defects). On the other hand, suppose that the signal from the laser channel and also the ratio of the signals from both channels remains nearly constant between neighboring measurement points (but nonetheless indicates a defect). One can conclude from this that one is encountering a local intensification of the micro-roughness, a so-called "high haze".

Further, the measurement results in the detector system (e.g. involving a plurality of sensors) can be separated into a plurality of channels, if the scattered light detector allows directional and/or location-dependent and/or frequency-dependent resolution. By a combination of a plurality of illumination devices and a plurality of detector channels, the information obtained from the scattered light is "multiplied". E.g. defects above the substrate surface will preferably scatter at shallow detection angles when illuminated at a shallow illumination angle, whereas embedded defects in the form of depressions or inclusions in the substrate will preferably scatter at steep, nearly perpendicular detection angles when illuminated at a steep illumination angle.

The various types of illumination according to the inventive method, and the various illumination devices according to the inventive inspection device system, can be configured independently of each other for various application situations. Thus, the extent of the image spot (thus the illuminated surface area) can be selected such that the productivity and sensitivity of the inspection device are optimized for a given application case. The geometry of the illumination can be arrived at, e.g., by changing the incident beam angle or changing the illumination optics. In this connection it should be noted that the necessary measurement time is determined by the smallest image spot. In the case of a large image spot, the measurement over a series of measurement points occurs in redundant pieces. Preferably the dimension of the smaller image spot is in the range 10-500 micron, which determines the width of the measurement trace of the long side of the image spot (in the direction transverse to the direction of rotation of the wafer).

BRIEF DESCRIPTION OF THE DRAWINGS

Additional objectives, functions, features, and advantages of the invention will be apparent from the following more detailed description with the aid of exemplary embodiments, with reference to the accompanying drawings.

DETAILED DESCRIPTION OF THE INVENTION

Figure 1:
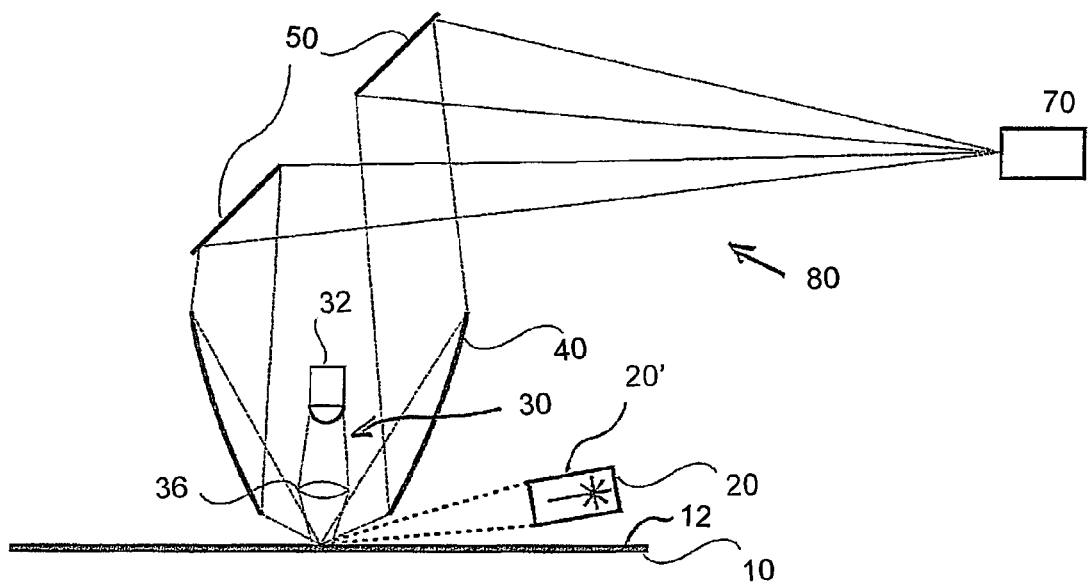
FIG. 1 is a schematic illustration of a first exemplary embodiment of the inventive inspection device.

FIG. 1 shows an embodiment of the inventive inspection device whereby the object (e.g. a wafer) 10 is examined for surface defects or irregularities. The inspection device has a first illuminating device 20 in the form of a laser 20' whereby a small beam is caused to impinge on the surface 12 of the wafer 10, creating a small image spot on said surface 12. The image spot caused by the illumination from the laser 20' on the surface 12 of the wafer 10 is a "streak" in the form of an elongated oval. The laser spectrum is such that the wavelength $\lambda_L$ of the laser light is typically in a narrow band monochromatic.

The inspection device further has a second illuminating device 30 having an LED 32 and a focusing optical system 36. The second illuminating device 30 is oriented perpendicularly to the surface 12 of the wafer 10, so that the image spot of a cylindrical light beam is circular. The optical system 36 focuses the light beams from the LED 32 onto an image spot which is appreciably larger than the image spot produced by the laser 20. The two image spots overlap. Stated more precisely, the smaller image spot from the laser 20' lies completely within the larger image spot from the second illuminating device 30. The spectrum of the LED light may be characterized by a wavelength $\lambda_D$ as a simplification, where $\lambda_D$ represents a relatively broad spectrum which may comprise several separate spectral bands.

The dimension of the image spot from the laser 20' of the illumination device 20 is typically 10-500 micron (500 micron maximum), with the aspect ratio being the result of the shallow angle of impingement of the light beam. Preferably, the dimension of the image spot from the second illumination device is 0.2-1 mm (0.2 mm minimum).

The light scattered from the irregularities in the object surface 12 is formed into an image on a sensor 70, via a focusing optical collecting system 40 and deflecting mirrors 50. The collecting optical system 40, deflecting mirrors 50, and sensor 70 form a first scattered light detector 80. In general, in the context of the present description the term "scattered light detector" should be understood to refer to one or more light-sensitive sensors, including upstream optical elements which guide the scattered light from the object surface 12 to a sensor 70. Various types of devices may be suitable candidates for use as the sensor, e.g. a photomultiplier, an avalanche diode, a photodiode or a CCD sensor (charge-coupled device sensor).

Figure 2:
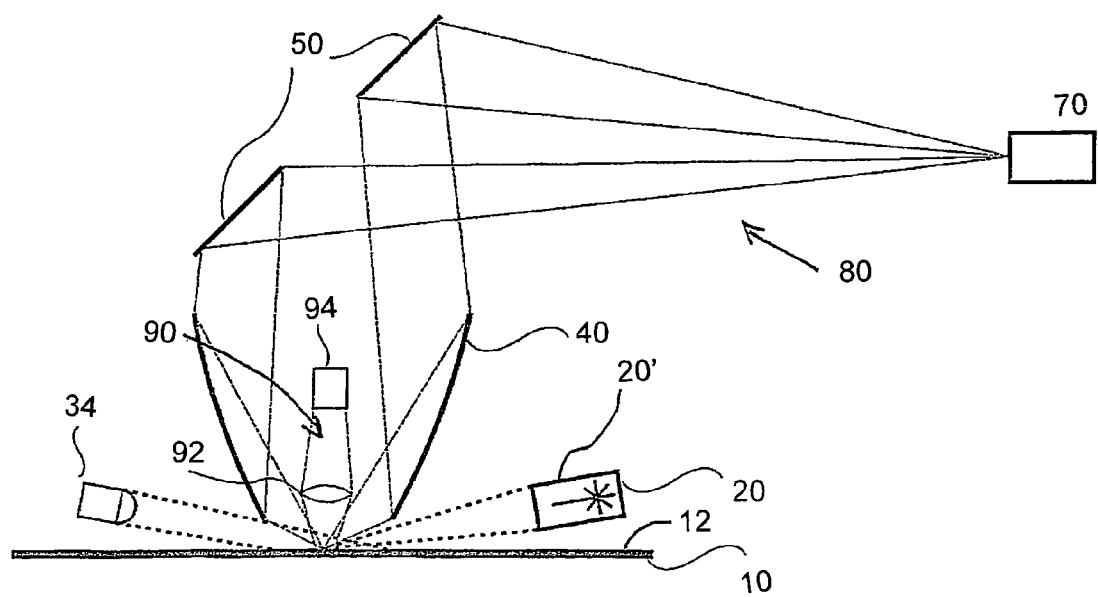
FIG. 2 is a schematic illustration of a second exemplary embodiment of the inventive inspection device.
Figure 3:
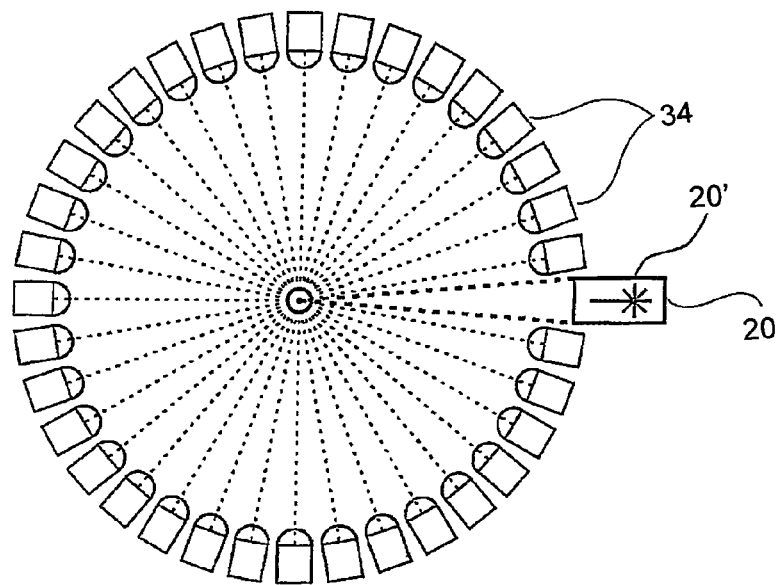
FIG. 3 is a plan view of the exemplary embodiment illustrated in FIG. 2.

In the exemplary embodiment according to FIGS. 2 and 3, the second illumination device is changed in that instead of a central light emitting diode (LED) 32 which sends illumination perpendicularly onto the wafer surface 12 one has a plurality of light emitting diodes 34 disposed around a circle (FIG. 3). These illuminate the wafer surface 12 along with the laser 20' of the first illumination device, at a low angle of incidence. The superposition of all of the LEDs 34 produces an image spot which is appreciably larger than the image spot from the laser 20'. As a result of the circular disposition and the plurality of the LEDs 34, the combined image spot from the second illumination device is nearly circular in shape and is also nearly isotropic. The plurality of LEDs causes a high light density of typically 1-100 mW/sq mm, with a very small extent ("very small space requirement").

The light beams of the LEDs 34 are limited on the upper side by the lower edge of the collecting mirror 40. This mirror thus serves as a collimator (of sorts) for the illumination from the second illumination device.

Although the structure of the first scattered light detector 80 is identical with that of the first embodiment, in comparison to FIG. 1 there is the difference that a second scattered light detector 90 is disposed at the location at which (FIG. 1) the LED 32 was disposed, with perpendicular observation of the object surface 12; the detector 90 has an optical collecting system 92 and a second sensor 94. The second detector 90 widens the range of the spherical angle of detected scattered light in the generally 90° direction, and enables determination of the differential scattered light intensity depending on the spherical angle (or spatial direction).

Figure 4:
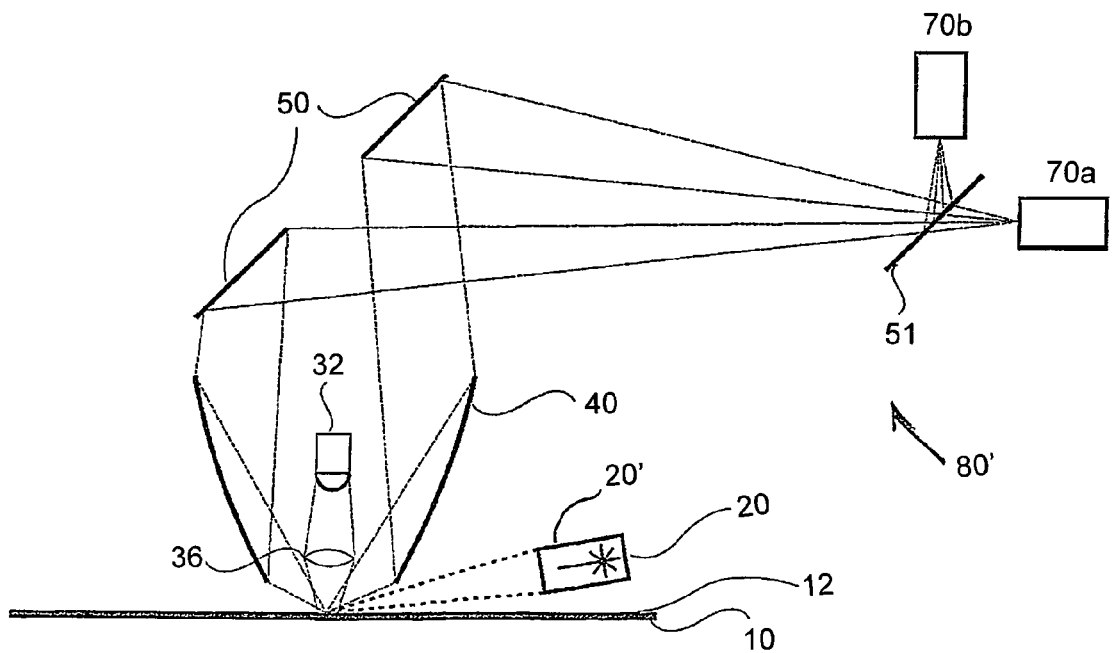
FIG. 4 is a schematic illustration of a third exemplary embodiment, similar to FIG. 1 but with 2 detectors and a wavelength-dependent beam divider.

The detector systems illustrated in the two exemplary embodiments may be replaced by more than two scattered light detectors, and/or a location-resolving scattered light detector system, in order to still better resolve the scattering angle information of the light reflected by the defects, and to be able to incorporate into this information defect analyses and defect classifications. Such a variant with frequency-dependent resolution is illustrated in the exemplary embodiments of FIGS. 4 and 5. The embodiment of the inventive inspection device according to FIG. 4 has, instead of a sensor 70 in the first scattered light detector 80 according to FIG. 1, a detector 80' having two sensors (70a, 70b) and a wavelength-dependent beam splitter 51. The optical collecting system 40 and deflecting mirrors 50 are the same as in the prior example. If the wavelengths $\lambda_L$ and $\lambda_D$ and the spectra of the first and second illumination devices are appreciably separated from each other, and the beam splitter 51 has an appropriate limit frequency, the splitter breaks up the scattered light into the two components (a component from the laser light and a component from the light generated by the LEDs), wherewith the splitter allows one of the components to pass through it (completely or substantially completely) and reflects the other component (completely or substantially completely). In this way, with a low angle of reflected (or scattered) light from the defects, a differentiation can be made depending on the incident light, simultaneously, for a single measurement point. This enables one to derive differentiated information about the form of the defect, in a rapid process.

Figure 5:
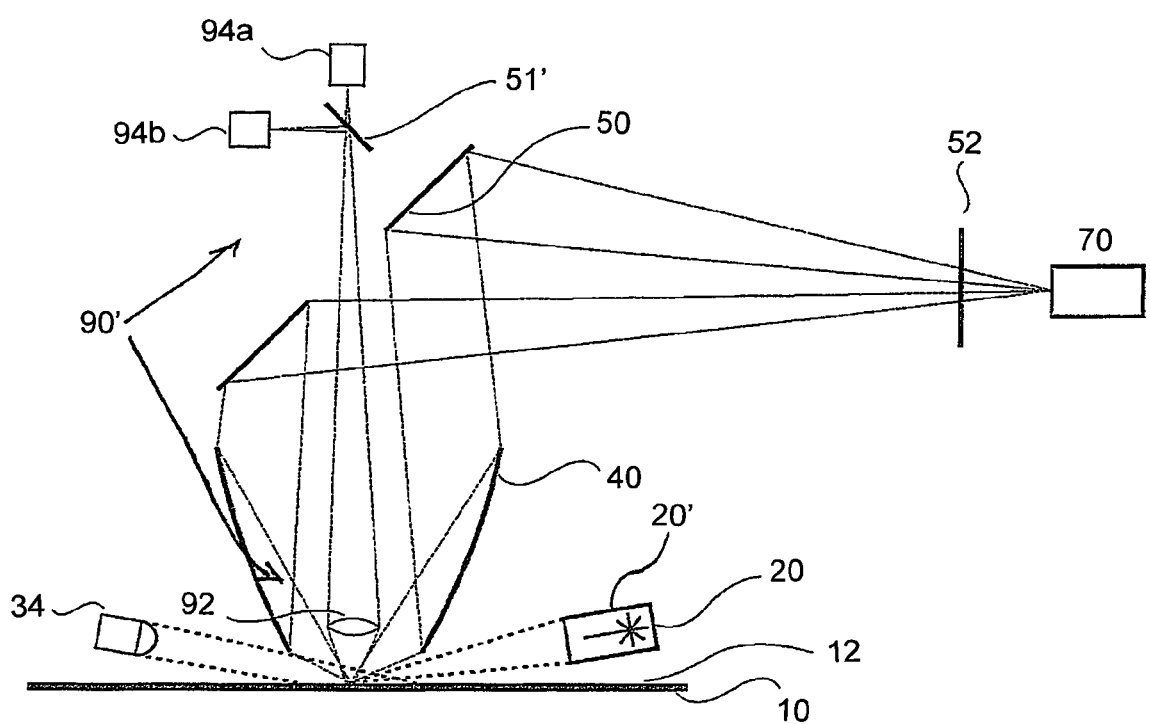
FIG. 5 is a schematic illustration of a fourth exemplary embodiment, similar to FIG. 2 but with 2 detectors and a wavelength-dependent beam divider.

The exemplary embodiment according to FIG. 5 has, instead of a second sensor 94 in the second scattered light detector 90 according to FIG. 2, a detector 90' having two second sensors (94a, 94b) and a wavelength-dependent beam splitter 51'. This device is also designed such that the beam splitter 51 resolves the scattered light into the two components (that from the laser light and that from the light generated by the LEDs), provided that the wavelengths $\lambda_L$ and $\lambda_D$ and the spectra of the first and second illumination devices are separated from each other. In this manner, as with the preceding example, with a high angle of reflected (or scattered) light from the defects, a differentiation can be made depending on the incident light, simultaneously, for a single measurement point. This enables one to derive differentiated information about the form of the defect, in a rapid process.

In order to arrive at a corresponding differentiation starting from a device according to FIG. 1 or 2, as an alternative to frequency-resolved measurement one may provide two measurements at each measurement point, one after the other, under different illumination conditions.

In place of the LEDs used in the exemplary embodiments for the second illumination devices, one may employ halogen lamps or discharge lamps. Also, for the large-area illumination with low energy density, it is possible to employ a laser beam, if one provides an expanding optical system (e.g. a cylindrical lens) in the beam path, such that at least the requirements of low anisotropy and a large image spot are met.

Drive means may be used for inspection of the entire surface of the object, namely to provide relative movement between
- the illumination and sensor optics; and
- the object surface.

In this connection, the wafer may be rotated around its center axis (which axis is perpendicular to the wafer surface 12), in known fashion, at a high speed. Typically, per rotation in the described manner c. 2000-8000 measurement points can be obtained for each of the two illumination systems. Ordinarily, a stepping motor or servo motor will be used as the drive means; to synchronize the measurements, one may use either the control signal of the stepping motor or a separate positioning sensor, e.g. an optical encoder.

List of Reference Numerals
10 Wafer.
12 Wafer surface; object surface.
20 First illumination device.
20' Laser.
30 Second illumination device.
32 LED.
34 LED.
36 Optical system.
40 Collecting optical system and collector mirrors.
50 Deflecting mirrors.
51 Beam splitter
51' Beam splitter.
70 Sensor.
70a Sensor.
70b Sensor.
80 First scattered light detector.
80' First scattered light detector.
90 Second scattered light detector.
90' Second scattered light detector.
92 Collecting lens.
94 Second sensor.
94a Second sensor.
94b Second sensor.

What is claimed is:

1. An inspection device for optical examination of object surfaces, comprising: a first illumination device and a second illumination device, for illuminating the object surface, and further having a scattered light detector disposed in a dark field of the first and second illumination devices, which detector is employed to detect light reflected and/or scattered from irregularities in the object surface, wherewith the first illumination device comprises a laser for illuminating a measurement point on the object surface; wherein the second illumination device is disposed and oriented to illuminate the same measurement point on the object surface but with a larger image spot, with the use of light of lower coherence and with less anisotropy than that of the laser.

2. The inspection device according to claim 1; wherein the second illumination device is set up so as to emit unpolarized light.

3. An inspection device according to claim 2; wherein the second illumination device has at least one broadband light source.

4. The inspection device according to claim 3; wherein the second illumination device has a light density of 1-100 W/sq mm.

5. The inspection device according to claim 4; wherein the second illumination device has a plurality of light sources in symmetrical disposition around the image spot on the object from the illumination.

6. The inspection device according to claim 5; wherein the second illumination device has a plurality of light sources in a circular or partial circular disposition around the image spot.

7. The inspection device according to claim 6; wherein the second illumination device has one or more light-emitting diodes (LEDs).

8. The inspection device according to claim 7; comprising said control means which alternately control the first and second illumination devices.

9. The inspection device according to claim 8; wherein the first and second illumination devices have spectral ranges which mutually differ, and the scattered light detector has a dichroic beam splitter or a spectral filter.

10. The inspection device according to claim 1 wherein the second illumination device has at least one broadband light source.

11. The inspection device according to claim 1 wherein the second illumination device has a light density of 1-100 W/sq mm.

12. The inspection device according to claim 1 wherein the second illumination device has a plurality of light sources in symmetrical disposition around the image spot on the object from the illumination.

13. The inspection device according to claim 1 wherein the second illumination device has a plurality of light sources in a circular or partial circular disposition around the image spot.

14. The inspection device according to claim 1 wherein the second illumination device has one or more light-emitting diodes (LEDs).

15. The inspection device according to claim 1 comprising said control means which alternately control the first and second illumination devices.

16. The inspection device according to claim 1 wherein the first and second illumination devices have spectral ranges which mutually differ, and the scattered light detector has a dichroic beam splitter or a spectral filter.

17. The inspection device according to claim 1, wherein the object is a wafer.

18. A method of inspection for optical examination of object surfaces comprising the steps of illuminating the object surface by a first illumination device and a second illumination device, wherewith the first illumination device illuminates a measurement point on the object surface by means of laser illumination, wherewith the light reflected and/or scattered from irregularities on the object surface is detected by means of a "scattered light detector" operating in a dark field of the first and second illumination devices; and illuminating with the second illumination device illuminates the same measurement point on the object surface as the laser beam, with a larger image spot, using light of lower coherence and lower anisotropy than that of the laser beam.

19. A method of inspection according to claim 18; wherein the first and second illumination devices are operated in alternation.

20. A method of inspection according to claim 19 wherein the first and second illumination devices are operated simultaneously but in different spectral ranges, wherewith the light emitted by the first and second illumination devices and reflected by the irregularities in the object surface is detected at spatially separate locations with the use of a dichroic beam splitter or a spectral filter.

* * * * *